(12) United States Patent
Forest et al.

(10) Patent No.: US 7,087,370 B2
(45) Date of Patent: Aug. 8, 2006

(54) KIT FOR VITRIFYING SPECIMENS

(76) Inventors: Katrina T. Forest, 1720 Vilas Ave., Madison, WI (US) 53711; Michelle T. Lane, 1661 W. Canal St. Apt. 324, Littleton, CO (US) 80120

( * ) Notice: Subject to any disclaimer, the term of this patent is extended or adjusted under 35 U.S.C. 154(b) by 265 days.

(21) Appl. No.: 10/241,061

(22) Filed: Sep. 10, 2002

(65) Prior Publication Data
US 2003/0113706 A1    Jun. 19, 2003

Related U.S. Application Data

(62) Division of application No. 09/416,992, filed on Oct. 13, 1999, now Pat. No. 6,500,608.

(60) Provisional application No. 60/104,266, filed on Oct. 14, 1998.

(51) Int. Cl.
*A01N 1/00* (2006.01)

(52) U.S. Cl. .................... 435/1.3; 435/260; 435/307.1; 435/975

(58) Field of Classification Search ................ 435/1.3, 435/1.1, 2, 260, 307.1, 374, 420; 62/51.1, 62/64
See application file for complete search history.

(56) References Cited

U.S. PATENT DOCUMENTS

| | | | | |
|---|---|---|---|---|
| 4,817,397 A * | 4/1989 | Grischenko et al. | ......... | 62/51.1 |
| 5,518,878 A | 5/1996 | Wilkins et al. | | |
| 6,057,151 A * | 5/2000 | Greenwood et al. | ..... | 435/307.1 |
| 6,381,967 B1 * | 5/2002 | Craig | ............................. | 62/64 |
| 6,500,608 B1 * | 12/2002 | Forest et al. | ................. | 435/1.3 |

FOREIGN PATENT DOCUMENTS

| DE | 39 12723 A1 | 10/1990 |
|---|---|---|
| DE | G 91 09 683.9 | 11/1991 |
| WO | WO 91/03935 | 4/1991 |

OTHER PUBLICATIONS

Rodgers, D. Cryocrystallography. Structure 1994 2(12)1135-1140.*
Hampton Research catalog printout from www.hamptonresearch.com Jan. 13, 2005.*
Lane, M. et al., "Live Births Following Vitrification of Hamster Embryos Using a Novel Containerless Technique," *Theriogenology*, vol. 51, Issue 1, p. 167, Jan. 1999.
Martino, A. et al., "Development into Blastocysts of Bovine Oocytes Cryopreserved by Ultra-Rapid Cooling," *Biology of Reproduction*, vol. 54, pp. 1059-1069, 1996.
Rodgers, D. W., "[13] Practical Cryocrystallography," *Methods in Enzymology*, vol. 276, pp. 183-203, 1997; published by Academic Press, Inc.
Parkin, S. et al., "Cryocrystallography Papers: Macromolecular Cryocrystallography: Cooling, Mounting, Storage and Transportation of Crystals," *J. Appl. Cryst.*, vol. 31, pp. 945-953, 1998; published by International Union of Crystallography.
Hope, H., "Cryocrystallography of Biological Macromolecules: a Generally Applicable Method," *Acta. Cryst.*, vol. 44, pp. 22-26, 1988; published by International Union of Crystallography.
Lane, M. et al., "Containerless vitrification of mammalian oocytes and embryos—Adapting a proven method for flash-cooling protein crystals to the cryopreservation of live cells," *Nature Biotechnology*, vol. 17, pp. 1234-1236, Dec. 1999; published by Nature America Inc.
Zhu, S. E. et al., "Cryopreservation of expanded mouse blastocysts by vitrification in ethylene glycol-based solutions," *J. of Reproduction and Fertility*, vol. 98, pp. 139-145, 1993; published by Journals of Reproduction and Fertility Ltd.
Rall, W. F. et al., "Ice-free cryopreservation of mouse embryos at −196° C by vitrification," *Nature*, vol. 313, pp. 573-575, Feb. 14, 1985.
Oberstein, N. et al., "Cryopreservation of Equine Embryos by Open Pulled Straw, Cryoloop, or Conventional Slow Cooling Methods." *Theriogenology*, vol. 55, pp. 607-613, 2001; published by Elsevier.
Lane, M. et al., "Vitrification of mouse and human blastocysts using a novel cryoloop container-less technique," *Fertility and Sterility*, vol. 72, No. 6, pp. 1073-1078, Dec. 1999; published by American Society for Reproductive Medicine.
J. Sambrook, et al., "*Molecular Cloning*", A Laboratory Manual, second edition, 1989, 1.32, 1.76-1.77, 1.86, Cold Spring Harbor Laboratory Press.
Przybylska, M., "A Novel Method of Mounting a Protein Crystal on a Surface Perpendicular to the X-Ray Capillary," *J. Appl. Cryst.*, vol. 21, pp. 272-273 (1988).
Rall, W. F. et al., "Ice-free cryopreservation and mouse embryos at −196° by vitrification," *Nature*, vol. 313, Feb. 14, 1985.
Grant & Hackh's Chemical Dictionary, fifth edition, McGraw-Hill Book Company, p. 584 (1987).
Massip, A. et al., "Cryoconservation de l'embryon bovin: techniques et resultats," *Ann. Med. Vet.*, vol. 131, 1987, pp. 515-528; published by Sciences Veterinaires, Universite Catholique de Louvain.
Dubochet, J. et al., "Cryo-Electron Microscopy of Vitrified Specimens," *Q. Rev. Biophys.*, vol. 21, pp. 129-228 (1988).

(Continued)

*Primary Examiner*—Ralph Gitomer
(74) *Attorney, Agent, or Firm*—Foley & Lardner LLP

(57) ABSTRACT

The present invention relates to systems for the vitrification of a biological specimen. The systems employ a transfer instrument such as a loop, containing a base medium that includes a cryoprotectant. The biological specimen which has undergone vitrification may be stored for a period of time, and then thawed at a later date. The thawed biological specimen remains viable. Preferred biological specimens according to the present invention are developmental cells.

12 Claims, 1 Drawing Sheet

OTHER PUBLICATIONS

Teng, T.-Y., "Mounting of Crystals for Macromolecular Crystallography in a Free-Standiing Thin Film," *J. Appl. Cryst.*, vol. 23, pp. 387-391 (1990).

Steponkus, P. et al., "Cryopreservation of *Drosophilia Melanogaster* Embryos," *Nature*, vol. 345, pp. 170-173 (1990).

Langis, R. et al., "Cryopreservation of Rye Protoplasts by Vitrification," *Plant Physiology*, vol. 92, 1990, pp. 666-671.

Szell et al., "Rapid Cryopreservation of Sheep Embryos by Direct Transfer into Liquid Nitrogen Vapour at −180° C," *Reproduction, Fertility and Development*, vol. 2, pp. 613-618 (1990).

W. Ray, Jr. et al., "Formation of Substrate and Transition-State Analogue Complexes in Crystals of Phosphoglucomutase after Removing the Crystallization Salt," *Biochemistry*, vol. 30, pp. 6875-6885 (1991).

W. Ray, Jr. et al., "Removal of Salt from a Salt-Induced Protein Crystal Without Cross-Linking. Preliminary Examination of "Desalted" Crystals of Phosphoglucomutase by X-Ray Crystallography at Low Temperature," *Biochemistry*, vol. 30, pp. 6866-6875 (1991).

Database BIOSIS, AN 1991: 496738, Riha et al., "Vitrification of Cattle Embryos by Direct Dropping into Liquid Nitrogen and Embryo Survival after Nonsurgical Transfer," *Zivocisna Vyroba*, 36 (2), pp. 113-119 (1991).

Tachikawa, S. et al., "Successful Vitrification of Bovine Blastocysts, Derived by In Vitro Maturation and Fertilization," *Molecular Reproduction and Development*, vol. 34, 1993, pp. 266-271; published by Wiley-Liss, Inc.

Zhu, S. E. et al., "Cryopreservation of expanded mouse blastocysts by vitrification in ethylene glycol-based solutions," *Journal of Reproduction and Fertility*, vol. 98, 1993, pp. 139-145; published by Journals of Reproduction and Fertility.

Rodgers, D. W., "Cryocrystallography," *Structure*, vol. 2, pp. 1135-1140 (1994).

Rall, W. F. et al., "High in vitro and in vivo survival of day 3 mouse embryos vitrified or frozen in a non-toxic solution of glycerol and albumin," *Journal of Reproduction and Fertility*, vol. 101, 1994, pp. 681-688; published by Journals of Reproduction and Fertility Ltd.

Kurata, K., "Vitrification of hematopoietic progenitor cells obtained from human cord blood," *Bone Marrow Transplantation*, vol. 14, 1994, pp. 261-263; published by Macmillian Press Ltd.

Kleywegt, G. et al, "Where Freedom is Given, Liberties are Taken," *Structure*, vol. 3, pp. 535-540 (1995).

Martino, A. et al., "Development into Blastocysts of Bovine Oocytes Cryopreserved by Ultra-Rapid Cooling," *Biol. of Reprod.*, vol. 54, pp. 1059-1069 (1996).

D. W. Rodgers, Practical Cryocrystallography, Methods in Enzymology, vol. 276, pp. 183-201 (1997).

Database BIOSIS, AN 1998: 101064, Vajta et al., "The Use of Vitrified Day 3 Embryos as Donors in Bovine Nuclear Transfer," *Cryo Letters*, vol. 18 (6), pp. 355-358 (1997).

Vajta, G. et al., "Vitrification of Porcine Embryos using the Open Pulled Straw (OP) Method," *Acta Veterinaria Scandinavica*, vol. 38 (4), pp. 349-352 (1997).

Vajta, G. et al., "Successful Vitrification of Early Stage Bovine in vitro Produced Embryos with the Open Pulled Straw (OPS) Method," *Cryo-Letters*, vol. 18, pp. 191-195 (1997).

Parkin, S. et al., "Macromolecular Cryocrystallography: Cooling, Mounting, Storage and Transportation of Crystals," *J. Appl. Cryst.*, vol. 31, pp. 945-953 (1998).

Walker, L. et al., "Cryocrystallography: Effect of Cooling Medium on Sample Cooling Rate," *J. Appl. Cryst.*, vol. 31, pp. 954-956 (1998).

Vajta, G. et al., "Open Pulled Straw (OPS) Vitrification: A New Way to Reduce Cryoinjuries of Bovine Ova and Embryos," *Molec. Repro. and Devel.*, vol. 51, pp. 53-58 (1998).

Otoi, T. et al., "Cryopreservation of mature bovine oocytes by vitrification in straws," *Cryobiology*, vol. 37, 1998, pp. 77-85; published by Academic Press.

Teng et al., "Cooling Rates During Flash Cooling," *J. Appl. Crystallogr.*, vol. 31, No. 2, pp. 252-257 (1998).

Kobayashi, S. et al., "Piglets Produced by Transfer of Vitrified Porcine Embryos after Stepwise Dilution of Cryoprotectants," *Cryobiology*, vol. 36, 1998, pp. 20-31; published by Academic Press, Inc.

\* cited by examiner

US 7,087,370 B2

KIT FOR VITRIFYING SPECIMENS

CLAIM OF PRIORITY

This application is a divisional of U.S. patent application Ser. No. 09/416,992, filed Oct. 13, 1999 now U.S. Pat. No. 6,500,608, which claims priority from U.S. Provisional Patent Application No. 60/104,266, filed Oct. 14, 1998.

GOVERNMENT SUPPORT

Statement as to Rights to Inventions Made Under Federally-Sponsored Research and Development Part of the work performed during development of this invention utilized U.S. Government Funds, specifically the National Institute of Child Health and Human Development, Grant No. HD22023. Therefore, the U.S. Government has certain rights in this invention.

TECHNICAL FIELD

This invention relates to a method for vitrification of a biological specimen, such that the biological specimen remains viable after it is thawed.

BACKGROUND OF THE INVENTION

The ability to cryopreserve oocytes, embryos, sperm and other similar biological specimens is critical to the widespread application of assisted reproductive technologies. However, due to the large volume of the cells and the high chilling sensitivity of oocytes and early embryos, cryopreservation techniques are not well developed in most species.

Traditionally, embryos are cryopreserved using "slow freezing techniques". Low concentrations of cryoprotectants and slow controlled rates of cooling usually in the range of 0.1–0.3° C./min. slowly dehydrate the cell during freezing to prevent intracellular crystallization. Because of this, cryopreservation of oocytes, embryos and other developmental cells using such procedures results in a reduced ability to both establish and maintain pregnancy following transfer. Oocytes are particularly susceptible to cryopreservation damage because of disruption of the metaphase spindle microtubule integrity during cooling.

Alternative prior cryopreservation methods have relied on vitrification with high concentrations of cryoprotectants, which when rapidly cooled result in a glass-like state. However, a disadvantage of this vitrification technique is that the cryoprotectants are very toxic to oocytes, embryos and other delicate developmental cells. Cryoprotectant toxicity can be minimized by increasing the cooling rate, which has been accomplished by plunging oocytes held on electron microscopy grids, or within thinly walled straws (known as open pulled straw) directly into liquid nitrogen. However, both of these procedures are cumbersome and recovery of embryos is problematic.

Therefore a need remains for a method for the vitrification of a biological specimen which is able to maximize the cooling rate of the cells of the specimen; maintain viability of the specimen during vitrification and subsequent thawing; prevent mechanical stress to the specimen; and provide ease of manipulations during cryopreservation and recovery.

SUMMARY OF THE INVENTION

The present invention relates to a method of vitrification of a biological specimen. According to the method of the present invention, a biological specimen is directly exposed to a freezing material. Upon exposure to the freezing material, the biological specimen undergoes vitrification. The biological specimen which has undergone vitrification may be stored for a period of time, and then thawed at a later date. The thawed biological specimen remains viable. Preferred biological specimens according to the present invention are developmental cells.

The present invention is also drawn to a method of vitrification of a biological specimen, which includes using a transfer instrument to place the biological specimen into a freezing material, such as liquid nitrogen, such that the biological specimen is directly exposed to the freezing material. The biological specimen then undergoes vitrification while held by the transfer instrument, with a loop being a preferred transfer instrument. The transfer instrument and biological specimen are then preferably kept within the freezing material, and transferred into a container which holds a freezing material. The container is preferably a vial. The vial is then sealed containing the freezing material, loop and the vitrified biological specimen, and may be cryopreserved until such time as the biological specimen is required for further use.

Another aspect of the present invention is the treatment of the biological specimen in a cryoprotectant prior to vitrification.

The invention also relates to a method for thawing a biological specimen which has undergone vitrification. The thawing methodology comprises the removal of the biological specimen from the freezing material wherein it has been cryopreserved, and placing the biological specimen in a warmed thaw solution. The thaw solution may be present in any suitable container, and is preferably located within a culture dish or a straw.

A further aspect of the present invention is a method of vitrification of developmental cells, wherein one or more developmental cells are placed directly into a freezing material, such that each developmental cell is directly exposed to the freezing material thereby undergoing vitrification, wherein the vitrified developmental cells, when thawed, cultured and implanted into suitable host organisms, will result in a fertility rate equal to that of the same developmental cells which had not been vitrified. Preferably, the developmental cells are contained within a loop when exposed to the freezing material.

The present invention also relates to a method of vitrification of a mammalian blastocyst or mammalian cleavage stage embryo which comprises placing one or more blastocysts or cleave stage embryos directly into a freezing material, such that each blastocyst or cleavage stage embryo is directly exposed to the freezing material thereby undergoing vitrification, wherein at least 80 percent, and more preferably, 90 percent, of the vitrified blastocysts or cleavage stage embryos will be viable after being thawed and cultured, preferably in the appropriate base medium. Preferably, the blastocyst or cleavage stage embryo is contained within a loop when exposed to the freezing material.

The present invention also relates to a method of vitrification of a horse embryo or pig embryo which comprises placing one or more embryos directly into a freezing material, such that each embryo is directly exposed to the freezing material thereby undergoing vitrification, wherein at least 25 percent, and more preferably, 50 percent, of the vitrified embryos will be viable after being thawed and cultured, preferably in the appropriate base medium. Preferably, the embryo is contained within a loop when exposed to the freezing material.

The present invention also relates to a kit for the vitrification of a biological specimen. The kit will generally contain instructions describing the vitrification of a biological specimen wherein the specimen is directly exposed to a freezing material. The kit will also include one or more optional ingredients, including, but not limited to, a transfer instrument, most preferably a loop, a vial which is of the proper size and shape to hold the loop and the vitrified specimen it contains, a base medium, a transfer solution, and a cryoprotectant.

The present invention is also drawn to biological specimens which have undergone vitrification by the methods of the present invention.

DETAILED DESCRIPTION

Figure 1:
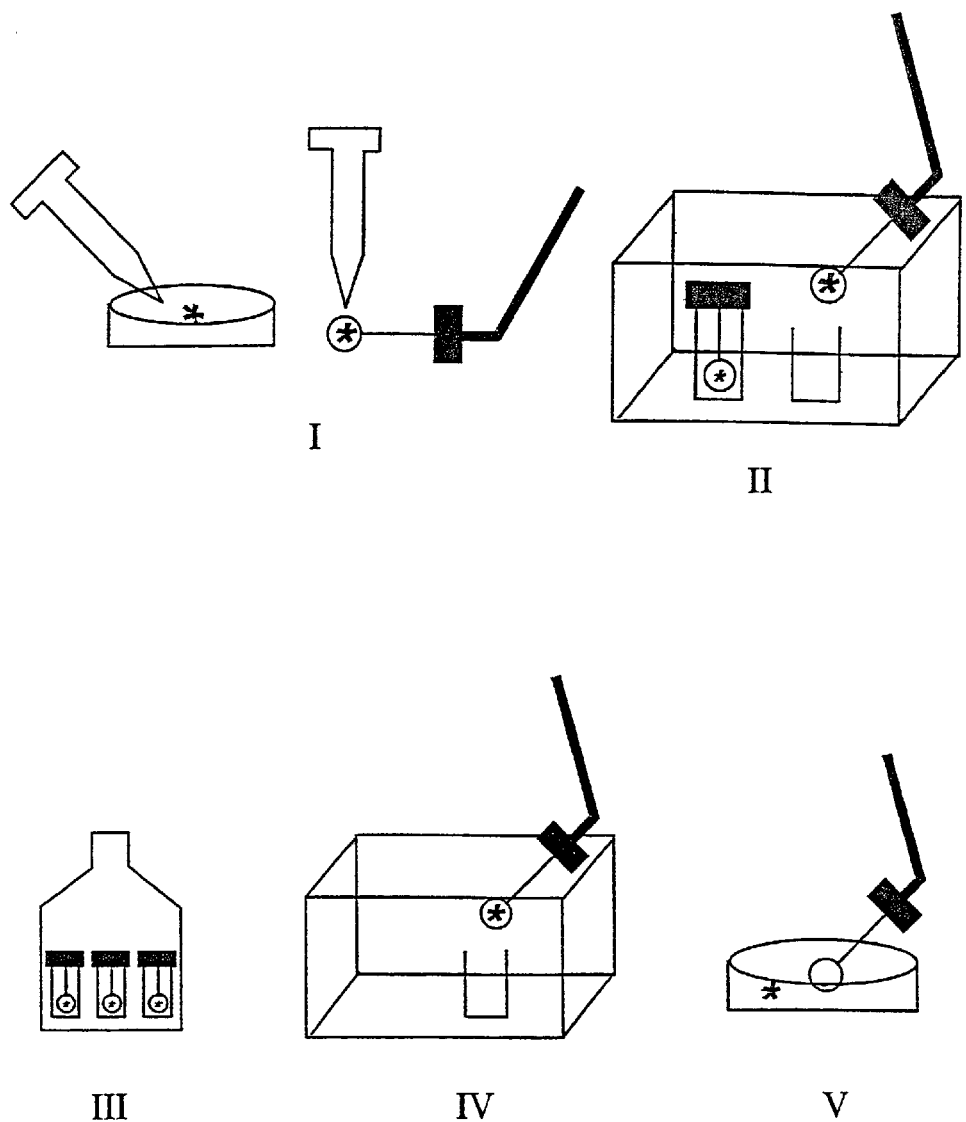
FIG. 1 is a schematic illustrating a method of vitrification of a biological specimen according to the present invention.

In the present application, the following terms are used throughout and are defined for the purposes of this application as follows:

Base Medium: A solid or liquid preparation made specifically for the growth, manipulation, transport or storage of the biological specimen present therein.

Cryopreservation: The preservation of a biological specimen at extremely low temperature.

Developmental Cells: A reproductive body of an organism that has the capacity to develop into a new individual organism capable of independent existence. Developmental cells include, but are not limited to, sperm, oocytes, embryos, morulae, blastocysts, and other early embryonic cells.

Directly Exposed: A biological specimen, including blastocysts and embryos, is "directly exposed" to a freezing material if the majority of the surface of the biological specimen, or the medium, solution or material in which the biological specimen resides, is allowed to come into direct contact with the freezing material.

Freezing Material: Any material, including but not limited to, liquid gases such as liquid nitrogen, liquid propane, liquid helium or ethane slush, which are capable of causing vitrification of a biological material.

Loop: An instrument for the manipulation of small biological samples, generally consisting of a rod shaped handle which holds a piece of nylon or metal wire such as platinum or nickel-steel, etc., formed into a closed loop at the free end.

Transfer Instrument: An instrument used to manipulate a biological specimen into a freezing material which is structured in such a fashion that it encircles and/or holds the biological specimen, and/or the medium, solution or material containing the biological specimen, in place during the vitrification process and/or allows ease of manipulation of the biological specimen within the freezing material, and wherein the transfer instrument allows the biological specimen to be directly exposed to the freezing material. The transfer instrument may be any such instrument generally known in the art, including, but not limited to a loop, net with handle, or paddle with handle instrument. The term "transfer instrument" as defined herein does not include either electron microscopy grids or straws (including both sealed straws and open pulled straws).

Viable: A biological specimen which is able to live and develop normally for a period of time.

Vitrification (Vitrify): A phenomenon wherein a biological specimen is rapidly cooled to very low temperatures such that the water in the specimen forms a glass-like state without undergoing crystallization.

The present invention is directed to a method for the vitrification of biological specimens, based on U.S. Provisional Patent Application No. 60/104,266, the entire contents of which is hereby incorporated by reference.

According to the method of the present invention, a biological specimen is placed directly into a freezing material such that the biological specimen is directly exposed to the freezing material. Upon exposure to the freezing material, the biological specimen undergoes vitrification. The biological specimen which has undergone vitrification may be stored for a period of time, and then thawed at a later date. The thawed biological specimen remains viable.

The present invention therefore has a number of uses. It may be used for animal husbandry, laboratory research, endangered species preservation, as well as for human assisted reproduction.

The biological specimen of the present invention can be any sort of viable biological specimen which is a living cell, but is preferably developmental cells, and more preferably mammalian developmental cells. Such cells can include, but are not limited to, sperm, embryos, blastocysts, morulae, and oocytes. Such preferred cells can be from any desired mammalian source, including but not limited to: humans; non-human primates such as monkeys; laboratory mammals such as rats, mice and hamsters; agricultural livestock such as pigs, sheep, cows, goats and horses; and zoologically important and/or endangered animals, etc. The use of other developmental cells from other living creatures are also within the scope of this invention, such as reptiles, amphibians, and insects such as *Drosophila*. Other suitable cells for use with the present invention include both stem cells, including human stem cells, and plant tissue cells. The following Examples describe the use of the present invention with a number of different cell types, including Hamster embryos, which are extremely sensitive to injury and therefore make a good model for any cryopreservation technique. The Examples also show the efficacy of the present invention with bovine oocytes and embryos which are known in the art to be extremely sensitive to chilling injury.

Preferably, the biological specimen is placed on a transfer instrument prior to vitrification. The transfer instrument can be any instrument that allows the biological specimen to be transported into a freezing material, while allowing the biological specimen to be directly exposed to the freezing material, allowing the biological specimen to be cooled very quickly, thus allowing the biological specimen to vitrify rather than form ice crystals within the cell, which would in turn ultimately disrupt cell walls and other vital cellular constituents.

The method of the present invention is in contrast to previous prior art methods wherein the biological specimen was enclosed within a container such as a sealed straw or open pulled straw, rather than being directly exposed to the freezing material.

Additionally, the present methodology differs from previous prior art methods which placed the biological specimen on open plates such as microscopy grids, which were unable to allow for facile manipulation of the specimen when contained within the freezing material, making handling of the specimen difficult and ultimately resulting in a poor recovery of the vitrified specimen. The present invention therefore allows better handling of the biological specimen during the vitrification process, and thereby solves the problem of specimen recovery known in prior microscopy grid vitrification methods.

The transfer instrument according to the present invention encircles and/or holds the biological specimen in place during the vitrification process, so that the biological material is not lost during the process. Therefore, the transfer instrument does not just allow the biological specimen to rest upon it, as with flat sheets or microscopy grids, but may actually help keep the specimen in place, as in the case with a loop via strong adhesion forces which surround the biological specimen, or medium, solution or material containing the specimen. Preferred transfer instruments of the present invention include, but are not limited to, loops, small nets with an attached handle and small spatulas. The spatulas, nets or loops may be modified in any way known in the art to help retain the biological specimen in place, including the placement of extra polymeric mesh or wire grids within the loop, net or spatula. In a preferred embodiment, the loop has an open loop and is attached via the rod-shaped end directly to the inside of a cap of a vial, the vial having the appropriate size and shape to allow the vitrified biological specimen and loop to be cryopreserved therein. It has been surprisingly and unexpectedly discovered that the use of a loop in the present vitrification methodology allows fast cooling rates, ease of visualization, facile manipulations and a high success rate of viability when the vitrified specimen is thawed and cultured.

In a preferred embodiment, the biological specimen is treated with a small amount of a cryoprotectant prior to vitrification. The methodology of the present invention also allows for a decrease in the time of exposure of the biological specimen to the solution phase of the cryoprotectant used, thus lowering the toxicity of the cryoprotectant to the biological specimen. Cryoprotectants, such as ethylene glycol, polyethylene glycol, dimethylsulfoxide, glycerol, propane diol, sugars, and methyl pentane diol, as well as others well known in the art, can be toxic to sensitive cells such as oocytes and embryos when used in large dosages during cryopreservation. The present invention allows for the use of any optional cryoprotectant to be present in solution phase in the presence of the biological specimen for shorter time periods than cryopreservation methods previously described in the art.

By allowing for quick cooling times, reduced time of exposure of solution phase cryoprotectants, and reliable retention and manipulation of the biological specimen, the present invention solves a long standing problem in the art of successful cryopreservation of sensitive biological specimens such as developmental cells. As further described in the Examples, the present invention has shown a success rate of vitrifying blastocysts or cleavage stage embryos such that, when thawed and cultured in the appropriate base medium, the cryopreserved blastocysts or cleavage stage embryos have a viability rate of 80 percent, preferably 90 percent, and preferably greater than 90 percent. Moreover, the present invention allows the vitrification of developmental cells, wherein the vitrified developmental cells, when thawed, cultured and implanted into suitable host organisms, will result in a fertility rate equal to that of developmental cells which are similarly implanted and which have not been cryopreserved. This helps solve a long-term problem in low pregnancy rates resulting from the use of cryopreserved developmental cells.

Additionally, the present methodology allows for the cryopreservation of biological specimens which in the past had resisted efforts of cryopreservation to result in a useful percentage of viable preserved specimens. Notably, pig embryos and horse embryos can now be vitrified according to the present invention, and wherein at least 25, 30, 35, 40, or 45 percent, and more preferably, 50, 55, 60, 65, 70 or 75 percent, of the vitrified embryos will be viable after being thawed and cultured.

According to the present invention, one or more biological specimens are collected by any means well known in the art, and are preferably transferred to a base medium. The base medium may contain one or more optional ingredients, such as a cryoprotectant to protect the biological specimen from cold and/or a viscosity increasing compound, to assist in maintaining the material within a transfer instrument, preferably a loop. The viscosity increasing compound can be any such compound known in the art, including, but not limited to, Ficoll, Percoll, hyaluronic acid, albumin, polyvinyl pyrrolidone (PVP), and glycerol.

According to the present invention, the biological specimen is preferably placed on a transfer instrument. The specimen may be placed in a base medium, and the transfer instrument, such as a loop or paddle, used to scoop the biological specimen from the base medium. In a preferred embodiment, the transfer instrument is a loop, and the loop is preferably dipped in base medium to form a thin film of the base material on the loop, and the biological material is deposited via pipette directly into the loop. If developmental cells such as embryos, sperm or oocytes are utilized as the biological specimen, one or more may be placed within each loop.

The transfer instrument containing the biological specimen is then quickly placed in a freezing material, such that the biological specimen is directly exposed to the freezing material, allowing vitrification of the biological specimen. Preferably, the time between pipetting the biological specimen onto the transfer instrument and the placement of the biological specimen into the freezing material is 45 sec. or less, more preferably 30 sec. or less. The freezing material may be liquid nitrogen, ethane slush, or any other freezing material well known in the art. Preferably, the biological specimen is held within the freezing material during all manipulations subsequent to vitrification, until the specimen is to be thawed.

The vitrified biological specimen is then transferred into a storage container. In a preferred embodiment, the transfer instrument is a loop which is attached to the inside of a vial cap. The vial is filled with the freezing material, and resides in the same reservoir as the freezing material used for vitrification of the biological specimen. After vitrification, the biological specimen, still contained within the loop, may be sealed in the vial without having been removed from the freezing material. The sealed vial, which contains the vitrified biological specimen and the loop within the freezing material, can then be cryopreserved indefinitely.

Thereafter, the biological specimen may be thawed, and the viable biological specimen may be further developed. Thawing is accomplished by removing the vial containing the vitrified biological specimen from any storage tank in which it resides, and quickly removing the transfer instrument containing the biological specimen from the vial, and plunging the transfer instrument and specimen into a thaw solution. In a preferred embodiment, the storage vial is placed in a reservoir containing a freezing material, preferably the same freezing material as contained within the vial. While within the freezing material, the vial is opened and the transfer instrument, containing the biological specimen, is removed and quickly plunged into the thaw solution. The thaw solution may be any solution or material that is sufficient to allow the biological specimen to thaw while preserving its viability, including but not limited to, media known in the art that is appropriate as a base medium for the particular biological specimen. After thawing, the biological specimen can be further manipulated in any appropriate manner known for the species and process for which the specimen is being utilized.

A preferred method of the present invention is further illustrated in accordance with FIG. 1. As shown in I, a biological sample in an appropriate base medium is applied directly to a loop or scooped directly into the loop. As shown in I, the loop is attached to a magnetic vial cap. Immediately thereafter, the loop is plunged directly into the freezing material contained within a reservoir, which as illustrated may be a insulated box filled with liquid nitrogen. Alternatively, the freezing material may be placed directly into the vial, and the biological specimen may be vitrified by being directly exposed to the freezing material within the vial itself, thereby eliminating the need for a separate reservoir. While under the liquid nitrogen, the loop is secured into the storage vial, with the vitrified biological specimen remaining within the loop. Multiple vials can be filled by keeping them upright in vial-sized holes within the reservoir, or, alternatively, single vials could be held under the nitrogen with a forceps or other tool. Multiple vials can then be cryopreserved indefinitely in any suitable container, such as a standard dewar, as illustrated in III. At any time thereafter, the loop may be removed from the vial while under a freezing material such as liquid nitrogen, as shown in IV, in the exact reversal of the vitrification procedure as described above. It is convenient, but not necessary, to use a reservoir of freezing material to surround the vial, before thawing, but the freezing material contained within the vial itself should be sufficient to keep the biological specimen cryopreserved during manipulation prior to being thawed. The biological specimen is then plunged directly into a thaw solution. The thaw solution may be contained in any manner which is convenient, including an open culture dish as shown in V, or in a straw for direct loading into a transfer gun. The biological specimen is instantly diluted into the thaw solution, and floats away from the loop. The biological specimen can then be cultured in any appropriate fashion known in the art.

Vitrification of sensitive biological specimens such as sperm, oocytes and embryos using the method of the present invention has advantages over conventional cryopreservation procedures in that the present method lacks any insulating layer between the biological specimen and the freezing material. This factor, coupled with the very small volume of less than 1–5 μl for the typical biological specimen used, or media, solution or other material containing the biological specimen used, results in both very rapid and uniform heat exchange during cooling. High rates of cooling prevent chilling injury to sensitive cells such as developmental cells. The extremely rapid cooling rate obtained with the present invention also substantially reduces the exposure time to any optional cryoprotectants used and thereby reduces their cytotoxicity to the specimen.

Other major benefits of the methods of the present invention include: an open system enabling ready visualization of the sample during manipulation; rapid freezing of a large number of samples with no need for expensive or complicated equipment; very straightforward labeling and storage; and trivial and instantaneous sample warming and recovery.

For applications that require a closed system such as human clinical applications, the use of standard cryovials enable them to be closed in standard plastic sheets, or alternatively, the release hole within the cryovial cap may be sealed shut, preventing any possible viral cross-transmission.

The ultimate test of viability of embryos following cryopreservation is the ability to establish and maintain a pregnancy resulting in normal fertile young. The hamster is a good model for this for two reasons. Firstly their sensitivity to the in vitro environment makes them a very sensitive model as evidenced by the fact that the inventors of the present invention are unaware of any report in the literature that has successfully produced hamster pups following cryopreservation using any method. Secondly, the hamster has a gestation period of only 16 days and sexual maturity is reached after 3–4 months. The following Examples demonstrate the success of the present methodology for cryopreservation of viable embryos which can then be thawed and used to produce normal young, resulting in a success rate of at least 90%.

Bovine embryos and in particular bovine oocytes are reported to be very sensitive to chilling injury. Furthermore, the high lipid content in the embryo has been linked to the increased sensitivity of bovine embryos to cryopreservation procedures. As shown in the following Examples, vitrification using the method of the present invention with oocytes and cleavage stage embryos of bovines allowed subsequent development to the morula/blastocyst stage in culture, with high percentage rates of successful hatching.

The present invention also relates to a kit for the vitrification of a biological specimen. The kit will generally contain instructions describing the vitrification of a biological specimen wherein the specimen is directly exposed to a freezing material. The kit will also include one or more optional ingredients, including, but not limited to, a transfer instrument, most preferably a loop, a vial which is of the proper size and shape to hold the loop and the vitrified specimen it contains, a base medium, a transfer solution, and a cryoprotectant.

This invention is illustrated further by the following nonlimiting Examples. All of the references listed in the application are hereby incorporated by reference.

EXAMPLE 1

Methodologies and Materials for Vitrification of Bovine and Hamster Oocytes and Embryos A. Media The medium used in the following Examples was Hamster Embryo Culture Medium-10 (HECM-10), prepared as described by Lane et al., *Mol. Reprod. Dev.* 50:443–450 (1998). For embryo collection and cryopreservation, a Hepes-buffered modification of HECM-10 where 20 mM NaHCO$_3$ was replaced with 20 mM Hepes (pH 7.35) was used. Cryoprotectant solutions were added to the medium immediately prior to use. Media for bovine embryo culture were G1.2 and G2.2, as taught by Gardner et al., *Hum. Reprod.* 13:3434–3440 (1998). All salts, carbohydrates, amino acids, dimethylsulfoxide (DMSO), ethylene glycol and sucrose were purchased from Sigma Chemical Company (St. Louis, Mo.). Bovine Serum Albumin was purchased from Bayer Diagnostics.

B. Hamster Embryo Collection and Culture

Hamster embryos were collected from super-ovulated females as previously described by Lane et al., *Mol. Reprod.*

Dev. 50:443–450 (1998). Hamster embryos were cryopreserved at either the pronuclear 1-cell or 2-cell stages. Hamster embryos were cultured in HECM-10 as taught by Lane et al., *Mol. Reprod. Dev.* 50:443–450 (1998). Cell number of resultant blastocysts was assessed by propidium iodide staining following triton treatment.

C. In Vitro Maturation/In Vitro Fertilization/In Vitro Culture (IVM/IVF/IVC) of Bovine Embryos Immature bovine oocytes were isolated from ovaries and matured as described by Krisher et al., *Biol. Reprod.* 60:1345–1352 (1999). Mature oocytes were either vitrified and thawed, or not subject to vitrification and thawing when used as controls, and fertilized in vitro, by the methods taught by Krisher et al., *Biol. Reprod.* 60:1345–1352 (1999). Following fertilization, putative zygotes were isolated and cultured in sequential media G1.2 and G2.2 for 72 hr. in each medium. After a total of 144 hr. development to the morula/blastocyst and blastocyst stages was assessed.

D. Vitrification Using Loop

Loops used for vitrification consisted of a nylon loop (20 μm width; 0.5–0.7 mm diameter) mounted on a stainless steel pipe held by epoxy to the lid of a cryovial (Hampton Research, Laguna Niguel, Calif.). Oocytes and embryos were vitrified using a 2-step loading with cryoprotectants. Initially oocytes and embryos were placed in cryoprotectant solution I which contained 10% DMSO and 10% ethylene glycol for 1–3 min. before being transferred to solution II, which contained 20% DMSO and 20% ethylene glycol, 10 mg/ml Ficoll (MW 400,000) and 0.65 M sucrose for approximately 20 sec. Cells are then transferred to the loop that had previously been dipped into solution II to create a thin-film. For hamster embryos, 10–12 embryos were placed on the loop, and for bovine embryos 3–6 embryos were placed on each loop. The embryos suspended in the nylon loop were then plunged directly into liquid nitrogen. By previously submerging the cryovial under liquid nitrogen, the loop containing the embryos was plunged into the cryovial containing liquid nitrogen and sealed under liquid nitrogen in one motion.

Oocytes and embryos were thawed using a 2-step dilution with sucrose. With the cryovial submerged under liquid nitrogen, the vial was opened and the loop containing cells was removed from the liquid nitrogen, and was then inserted directly into a well of the base medium containing 0.25 M sucrose. The oocytes/embryos immediately fell from the loop into the thaw solution. Oocytes were moved from this solution after 2 min. and transferred to base medium containing 0.125 M sucrose for a further 5 min. Subsequently, oocytes/embryos were washed twice in the base medium for 5 min. and were then returned to culture.

E. Vitrification Using Open Pulled Straw Technique

For comparison purposes, hamster embryos were vitrified using the open-pulled straw (OPS) technique described by Vajta et al., *Cryo-Letters* 18:191–195 (1997). Ten-twelve embryos were exposed to a 2-step loading of cryoprotectants consisting of ethylene glycol and DMSO at the same concentrations as above. Embryos were pipetted into a 1 μl drop of the second cryopreservation solution and then loaded into a pulled straw using capillary action and the straw containing the embryos was plunged directly into liquid nitrogen. For thawing, embryos were expelled from the straw by pressure build-up during warming and thawed as above.

F. Embryo Transfer

Hamster morulae/blastocysts were transferred to day 3 (−1 day asynchronous) pseudo-pregnant recipients. Eight embryos were transferred to each uterine horn. On day 14 of pregnancy some animals were euthanized and implantation and fetal development rates determined. The remaining females were allowed to litter on day 16 of pregnancy and the number of pups was recorded soon after birth.

G. Statistical Analyses

Differences in development among treatments were assessed using linear-logistic regression where the distribution was binomial (Glim 4.0, Numerical Algorithms Group, Oxford, UK). Day of experiment was fitted as a factor. Differences in cell numbers were assessed using Analysis of Variance as both Gaussian normality and equal variances were confirmed. Multiple comparisons between treatments were assessed by Bonferroni's procedure for multiple comparisons.

EXAMPLE 2

Vitrification and Subsequent Development of Hamster Embryos

Hamster 2-cell embryos were vitrified using a loop according to the method of the present invention, and compared with results of control embryos exposed to cryoprotectant or embryos vitrified using the OPS method, as described in Example 1. Hamster embryos were collected from the oviduct, and allocated to either the control, loop or OPS vitrification. Significantly more embryos developed to the morula/blastocyst and blastocyst stage when vitrified within the loop compared to those vitrified using OPS, as shown below in Table 1.

Significantly fewer 2-cell embryos were able to continue development to the morula/blastocyst or blastocyst stages in culture following vitrification by either technique compared to control embryos, as shown in Table 1. However, the cell numbers of the blastocysts (an indicator of cleavage rates) resulting from vitrified 2-cell embryos were statistically equivalent to 2-cell embryos that were not vitrified, as shown in Table 1. Rat 2-cell embryos were also successfully vitrified using the loop and could develop normally after thawing with cleavage rates of 75%, similar to control embryos (n=10).

To further assess the ability to vitrify sensitive embryos, the experiment was repeated with 1-cell embryos, although the length of time that the 1-cell embryos were exposed to the initial dilution of cryoprotectant was reduced from 2 min. to 1 min. Preliminary studies demonstrated that a 2 min. exposure (without vitrification) of 1-cell embryos to the cryoprotectant solutions severely reduced development. Again embryos were collected from the oviduct and allocated to either the control, loop or OPS vitrification.

Hamster 1-cell embryos were able to cleave and continue development in culture to the morula/blastocyst stage following vitrification with the loop, as shown in Table 1. Developmental rates after vitrification were significantly better for embryos vitrified using the loop compared to those vitrified using OPS (Table 1). Hamster oocytes were also able to be successfully vitrified using the loop (n=20) and subsequently fertilized and developed to the morula/blastocyst stage at rates of around 10%, comparable to control non-cryopreserved oocytes.

TABLE 1

Development of Hamster Embryos in Culture Following Vitrification

| Stage of Development | Treatment | M/B (%) | B (%) | Blastocyst Cell Number (mean ± sem) |
|---|---|---|---|---|
| 1-cell | Control | 79.5 | 30.1 | 18.9 ± 3.1 |
|  | Loop | 39.8[a] | 15.5[a] | 11.9 ± 1.1[a] |
|  | OPS | 22.0[b] | 5.0[b] | 9.2 ± 1.2[b] |
| 2-cell | Control | 98.5 | 94.2 | 24.1 ± 2.8 |
|  | Loop | 64.2[a] | 43.1[a] | 19.7 ± 1.8[a] |
|  | OPS | 50.5[a] | 29.6[b] | 19.6 ± 1.4[a] |

M/B morula/blastocyst development
B blastocyst development
N = at least 100 embryos cultured per treatment for 1-cell embryos (4 replicates) and at least 400 embryos per treatment for 2-cell embryos (8 replicates)
[a]significantly different from control ($P < 0.05$)
[b]significantly different from control and from loop vitrification ($P < 0.05$).

EXAMPLE 3

Viability of Hamster 1-Cell and 2-Cell Embryos Following Vitrification

Hamster embryos were vitrified using either the loop method or by OPS. Following warming, embryos were cultured to the morula/blastocyst stage (both vitrified and control embryos) before transfer to pseudo-pregnant recipients. There was no difference in the viability of morula/blastocyst stage embryos that had been previously vitrified at the 2-cell stage to implant and develop to a viable fetus compared to control embryos that were not cryopreserved, as shown below in Table 2. However, significantly fewer embryos were able to implant and develop to a viable fetus when vitrified using OPS, as shown in Table 2. Two additional females that received morulae/blastocysts which were vitrified at the 2-cell stage using the loop were allowed to litter and 5 normal pups were born. These pups developed into morphologically sound and fertile adults.

Similarly, for hamster 1-cell embryos, implantation and fetal development were not affected by vitrification using the loop, as shown in Table 2. No embryos vitrified using OPS were transferred due to the low survival rates in culture observed in the previous experiment. Again two females which received morulae/blastocysts vitrified at the 2-cell stage using the loop were allowed to litter and a total of 9 pups were born. One pup was eaten by the mother 6 to 9 days after birth. The remaining pups developed into morphologically sound and fertile adults.

TABLE 2

Development of Hamster Embryos in utero Following Vitrification

| Stage of Development for Vitrification | n | Method | Implantation N (%) | Fetuses N (%) |
|---|---|---|---|---|
| 1-cell | 20 | Control | 8(40) | 6(30) |
|  | 17 | Loop | 7(41) | 5(29) |
| 2-cell | 40 | Control | 34(85) | 26(65) |
|  | 72 | Loop | 39(54)[a] | 36(50) |
|  | 112 | OPS | 48(43)[a] | 40(36)[a] |

[a]significantly different from control embryos ($P < 0.05$)

EXAMPLE 4

Vitrification of Bovine Oocytes, Cleavage Stage Embryos and Blastocysts

To determine the ability of the vitrification method of the present invention to successfully vitrify embryos with different cellular properties, bovine oocytes and embryos were vitrified as taught in Example 1, and their survival and subsequent development assessed, and the results shown in Table 3. Oocytes and embryos were allocated to either the control group or to loop vitrification using the methodology of the present invention. In vitro produced bovine blastocysts were successfully vitrified using the loop with more than 80% of expanded blastocysts being able to both re-expand and hatch following vitrification, as shown in Table 3. Culture of control blastocysts resulted in 100% hatching after 48 hr. of culture. Furthermore, 75% of completely hatched blastocysts could also be successfully vitrified using loop vitrification. Eight-cell bovine embryos vitrified using the vitrification method of the present invention could be vitrified and warmed with subsequent survival rates (assessed by development to the morula/blastocyst and blastocyst stages) equivalent to those obtained for fresh embryos that had not been cryopreserved, as shown in Table 3. Vitrification of embryos at the 4-cell stage resulted in slightly reduced survival rates compared to the fresh embryos, however many were able to complete normal development to the morula/blastocyst stage, as shown in Table 3. Bovine oocytes are extremely sensitive to chilling damage and few reports have demonstrated any success following cryopreservation. In vitro matured bovine MII oocytes were successfully vitrified using the loop. Vitrified and warmed oocytes were subsequently fertilized and of these 33% continued development to the morula/blastocyst stage (n=42).

TABLE 3

Development of Bovine Embryos in Culture Following Vitrification

| Stage of Development | Treatment | 8-Cell at 72 Hr. (%) | M/B at 144 Hr. (%) | B at 144 Hr. (%) | HB at 168 Hr. (%) |
|---|---|---|---|---|---|
| 4-cell | Control | 0 | 46 | 15 | n/d |
|  | Loop | 4 | 24 | 16 | n/d |
| 8-cell | Control | n/a | 59 | 50 | n/d |
|  | Loop | n/a | 52 | 41 | n/d |
| Blastocyst | Control | n/a | n/a | n/a | 100 |
|  | Loop | n/a | n/a | n/a | 80.5 |

M/B, morula/blastocyst development
B blastocyst development
HB hatched blastocyst development
n/a not applicable
n/d not determined

EXAMPLE 5

Methodologies and Materials For Vitrification of Human and Mouse Blastocysts

A. Culture Media

Media for embryo culture was G1.2 and G2.2 (IVF Sciences Scandinavian, Gothenburg, Sweden). Media for embryo collection was a HEPES-modification of G1.2 (H-G1.2) and the base medium for cryopreservation and thawing was a HEPES-buffered modification of G2.2 without amino acids and vitamins (H-G2.2). In both cases the media were modified by replacing 20 mM $NaHCO_3$ with 20 mM HEPES and adjusted to pH 7.35.

B. Mice

Embryos were collected from 4–6 week old F1 (C57BL6xCBa) females. Females were stimulated with 5 iu of pregnant mare's gonadotrophin (Sigma Chemical Co., St. Louis, Mo.) and 48 hr. later with 5 iu of human chorionic gonadotrophin (hCG; Sigma Chemical Co.). Following the hCG injection females were placed with males of the same strain and the following morning the presence of a vaginal plug indicated that mating had taken place. Zygotes were collected at 22 hr. post-hCG and denuded from surrounding cumulus by incubation in H-G1.2 with 0.5 mg/ml hyaluronidase for less than 1 min. Zygotes were washed twice in H-G1.2 and placed in culture.

C. Mouse Embryo Culture

Mouse zygotes were cultured in groups of 10 in 20 µl drops of medium G1.2 at 37° C. in an humidified atmosphere of 5% $CO_2$ in air. After 48 hr. of culture, 8-cell embryos were washed 3 times in medium G2.2 and cultured for a further 48 hr. in 20 µl drops of medium G2.2. Blastocyst development was assessed after 96 hr. of culture.

D. Human Embryo Culture

The culture system for blastocyst growth was done according to Gardner et al., *Hum. Reprod.* 13:3434–40 (1998). Following oocyte retrieval, cumulus enclosed oocytes were incubated in Ham's F-10 supplemented with fetal cord serum (FCS) for insemination. Semen was prepared with a 50–70–95 discontinuous gradient or minigradient method (Pure Sperm, Nidacon, Gothenburg), depending on the initial semen parameters. The resulting pellet was washed in Ham's F-10. For normal insemination, to each oocyte, 50–100,000 sperm/mL were added. If intracytoplasmic injection (ICSI) was performed, oocytes were denuded using hyaluronidase and drawn pipettes. Each mature oocyte was placed in a 6 µl droplet of phosphate buffered saline supplemented with 15% FCS. The partner's sperm was placed in a 6 µl droplet of PVP (IVF Sciences Scandinavian). All droplets were overlaid with Ovoil (IVF Sciences Scandinavian). ICSI was performed on a Nikon inverted microscope with Narishige micromanipulators. Injected oocytes were then rinsed and placed in tubes of G 1.2 until fertilization was assessed. Fertilization was assessed 15–18 hr. post insemination or ICSI. Cumulus and corona cells were removed by dissection with 27-gauge disposable needles in an organ culture dish. Resulting 2 pronuclear embryos were washed well and subsequently cultured in groups of 2–3 in G1.2 medium in 1-mL Falcon culture tubes in 5% $CO_2$ in air.

After 48 hr. of culture, embryos were rinsed 3 times and cultured for a further 72 hr. Blastocysts on day 6 that were not considered of good enough quality to cryopreserve by previous methods known in the art, i.e. not fully expanded or with poor inner cell mass development, were donated for vitrification by the method of the present invention.

E. Vitrification Using a Loop

Loops used for vitrification consisted of a nylon loop (20 µm width; 0.5–0.7 mm diameter) mounted on a stainless steel pipe inserted into the lid of a cryovial. The loops were purchased mounted (Hampton Research, Laguna Niguel, Calif.) and then epoxied into vials. A metal insert on the lid enables the use of a handle with a small magnet for manipulation of the loop if desired.

Blastocysts were vitrified using a 2-step loading with cryoprotectants. Initially blastocysts were placed in cryoprotectant solution I which contained 10% DMSO and 10% ethylene glycol for 2 min. before being transferred to solution II, which contained 20% DMSO and 20% ethylene glycol, 10 mg/ml Ficoll (MW 400,000) and 0.65 M sucrose for around 20 sec. These concentrations of cryoprotectants and length of exposure have previously been demonstrated to be optimal for the vitrification of both rodent and domestic animal embryos using the loop procedure. While blastocysts are in cryoprotectant solution I, the loop is dipped into cryoprotectant solution II to create a thin film on the loop. The blastocysts were then transferred from solution II onto the film of cryoprotectant on the loop. The loop containing the blastocyst was then plunged into the cryovial which is submerged and filled with liquid nitrogen. By previously submerging the cryovial under liquid nitrogen, the loop containing the blastocysts could be plunged into the cryovial containing liquid nitrogen and sealed under liquid nitrogen in one motion. The vials were stored in standard canes.

Blastocysts were thawed using a 2-step dilution with sucrose. With the cryovial submerged under liquid nitrogen the vial was opened and the loop containing blastocysts removed from the liquid nitrogen and placed directly into a well of the base medium containing 0.25 M sucrose. The blastocysts immediately fell from the loop into the thaw solution. Blastocysts were moved from this solution after 2 min. and transferred to base medium containing 0.125 M sucrose for a further 3 min. Subsequently, blastocysts were washed twice in the base medium for 5 min. and were then returned to culture.

Following vitrification, mouse and human blastocysts were cultured in medium G2.2 for 6 hr. to assess re-expansion before assessment of blastocyst outgrowth. A 6 hr. incubation was chosen as this is the normal time period used for the assessment of thawed blastocysts prior to transfer.

F. Assessment of Blastocyst Outgrowth

Both mouse and human blastocysts were assessed for outgrowth as a marker of subsequent viability. Blastocysts were transferred to medium G2.2 supplemented with 10% fetal cord serum to assess blastocyst attachment and outgrowth. Blastocysts were cultured in 4 well plates (Nunclon, Denmark) previously coated with 0.1% gelatin in 500 µl drops at 37° C. in 5% $CO_2$ in air for 48 hr. Blastocyst hatching and attachment were assessed after 24 hr. and outgrowth assessed after a further 24 hr. of culture. Outgrowth of inner cell mass (ICM) and trophectoderm was given a score between 0 and 3 based on the amount of outgrowth, where 0 was no growth and 3 was extensive growth as described by Spindle and Pederson, *J. Exp. Zool.*, 186:305–318 (1972).

G. Assessment of Blastocyst Viability in Mice

Viability of mouse blastocysts following vitrification was assessed by transfer to pseudo-pregnant recipients. Following warming, blastocysts were cultured for 6 hr. in medium G2.2 prior to transfer. All blastocysts that re-expanded after the 6 hr. period were pooled and blastocysts for transfer randomly selected. Six blastocysts were transferred to each uterine horn. On day 15 of pregnancy, implantation, fetal development and fetal weights were assessed. Non-cryopreserved blastocysts served as the control.

H. Statistical Analyses

Differences in hatching, attachment and viability following vitrification were assessed by Chi-square analysis with Yates Correction. Data for outgrowth of both the ICM and trophectoderm were initially subjected to a Kolmogorov- Smirnov test to determine the normality of the data. An F-test was then used to assess that the two groups of data had equal variances. Once the normality and equal variances were established differences in outgrowth were assessed by Student's t-test.

EXAMPLE 6

Vitrification of Mouse Blastocysts

A total of 160 mouse blastocysts were vitrified using a loop according to the present invention. Following vitrification, 100% of these blastocysts were able to re-expand in culture. There was no difference in the ability of vitrified blastocysts to hatch and attach in culture compared to control embryos, as shown in Table 4. Similarly, there was no difference in the ability of either the ICM or trophectoderm to outgrow in culture between the control and vitrified blastocysts, as demonstrated in Table 4.

Following vitrification and thawing, 60 blastocysts were transferred to pseudo-pregnant recipients and their viability compared to sibling control blastocysts that were not cryopreserved. There was no difference in the ability of vitrified blastocysts to implant and develop to a fetus compared to control blastocysts. Resultant fetal weights were also similar for blastocysts that were vitrified (0.245±0.021 g) compared to control blastocysts (0.250±0.017 g). All fetuses resulting from both vitrified and control blastocysts were morphologically normal. Additionally a recipient female that received 8 vitrified blastocysts (4 per uterine horn) was allowed to litter. Three morphologically normal pups were born.

TABLE 4

Effect of Loop Vitrification of Mouse Blastocysts on Re-Expansion and Outgrowth

| Treatment | Study group | |
|---|---|---|
| | Control | Vitrified blastocysts[1] |
| Re-expansion (%) | — | 100 |
| Hatching (%) | 87.5 | 95.5 |
| Attachment (%) | 78.1 | 85.9 |
| ICM outgrowth (means ± SEM) | 2.21 ± 0.10 | 2.17 ± 0.09 |
| trophectoderm outgrowth (means ± SEM) | 2.00 ± 0.09 | 2.14 ± 0.09 |

[1]there was no difference between control and vitrified blastocysts for any parameter measured.
n ≧ 100 for both control and vitrified blastocysts

EXAMPLE 7

Human Blastocyst Vitrification

Eighteen human blastocysts between minimally to semi-expanded were vitrified using a loop according to the methodology of the present invention. Of these 11 (83.3%) re-expanded in culture. Ability to hatch in culture and outgrowth of the ICM and trophectoderm were similar for blastocysts that were vitrified and control blastocysts that were not cryopreserved, as shown in Table 5.

TABLE 5

Effect of Loop Vitrification of Human Blastocysts on Re-Expansion and Outgrowth

| Treatment | Study group | |
|---|---|---|
| | Control n = 12 | Vitrified blastocysts[1] n = 18 |
| Re-expansion (%) | — | 83.3 |
| Hatching (%) | 63.6 | 73.3 |
| Attachment (%) | 36.0 | 60.0 |
| ICM outgrowth (means ± SEM) | 2.0 ± 0.2 | 1.7 ± 0.2 |
| trophectoderm outgrowth (means ± SEM) | 1.7 ± 0.2 | 2.0 ± 0.2 |

[1]there was no difference between control and vitrified blastocysts for any parameter measured.

EXAMPLE 8

Vitrification of 8 Day Bovine Blastocyst

The following solutions were used in this Example:

Freeze Solutions:
  Solution 1: Base medium (as taught in Example 1) containing 10% ethylene glycol and 10% DMSO
  Solution 2. Base medium containing 0.65 M sucrose and 20% ethylene glycol and 20% DMSO and 10 mg/ml Ficoll Thaw solutions:
  Solution 1: Base medium with 0.25 M sucrose
  Solution 2: Base medium with 0. 125M sucrose
  Solution 3: Base medium
  Solution 4: Base medium Bovine blastocysts were produced according to the methods described in Example 1. The blastocysts were all expanded to some degree prior to vitrification. The blastocysts were pipetted using standard equipment onto a loop that had been dipped into Freeze Solution 2. Each loop contained a single blastocyst. The loops containing the blastocysts was then treated for 2 min. in Freeze Solution 1, followed by 30 sec. of treatment in Freeze Solution 2 which included a viscosity solution of Ficoll and then immediately plunged directly into liquid nitrogen and vitrified. The blastocysts were kept frozen in liquid nitrogen for 30–90 min. and then thawed.

To thaw the blastocysts, the blastocysts and the loop in which they were vitrified were placed for five min. each in Thaw Solutions 1–4 sequentially.

Of the 13 blastocysts that were vitrified and thawed according to the present invention, 9 of the blastocysts hatched after being cultured after 48 hr.

A second set of 4 blastocysts were vitrified, thawed and cultured as described above, and all 4 blastocysts successfully hatched after being cultured for 48 hr.

A third set of 8-day bovine blastocysts were produced by the methods described in Example 1. A total of 12 blastocysts were used, and 2 expanded blastocysts were placed in each loop. The blastocysts were subject to vitrification, thawing and culturing as described, except the thawing process was conducted according to the following regime. Two min. in Solution 1; 5 min. in Solution 2; 5 min. in Solution 3 and 5 min. in Solution 4. After being cultured for 48 hr., 11 of the blastocysts had hatched.

EXAMPLE 9

Vitrification of Nine Day Bovine Blastocysts

Bovine blastocysts were produced according to methods described in Example 1 and vitrified as described in Example 8. The blastocysts were then thawed and cultured as described in Example 8. After 48 hr., 80% of the blastocysts had hatched.

EXAMPLE 10

Vitrification of Seven Day Bovine Blastocysts

Seven day bovine blastocysts were produced as described in Example 1 and cultured using G1.2/G2.2 as described in Example 1. A total of 20 blastocysts were vitrified and thawed according to the method described in Example 8 and frozen for 2 hr. with 2 to 3 blastocysts per loop. The blastocysts were then thawed and cultured as described in Example 8. After the thawed blastocysts were cultured for 48 hr., 15 of the 20 blastocysts had hatched and 2 had re-expanded.

A second experiment was conducted with seven day blastocysts according to the procedures described above, with 1 to 2 blastocysts per loop. After 48 hr. of culture, 29 of the 33 vitrified blastocysts had hatched.

EXAMPLE 11

Vitrification of Bovine Oocytes

In this Example, the vitrification of bovine oocytes using methodology of the present invention was compared to oocytes which were vitrified using the known open pulled straw (OPS) methodology and also to control oocytes which had not been frozen. The oocytes which were to be vitrified were treated for 35 sec. in Solution 1 and for 30 sec. in either Solution 2 alone or Solution 2 plus a viscosity solution, using the Solutions described in Example 8. The oocytes were then frozen either 1–3 per straw or 1 to 3 per loop by plunging them into liquid nitrogen. After vitrification, all oocytes were thawed according to the following regime: 1 min. in Solution 1; 5 min. in Solution 2; 5 min. in Solution 3; and 5 min. in Solution 4, using the Solutions of Example 8. The bovine oocytes were then returned to maturation media for 2 hr. and then fertilized in the normal fashion. After one day, the oocytes were moved to medium G1.2 as described in Example 1. After 4 days, the cleaved embryos were moved to fresh medium G1.2, as described in Example 1. The control oocytes showed 37.5% cleavage, the oocytes which had undergone vitrification according to the current methodology showed 19% cleavage, and those which were vitrified using the OPS methodology showed 14% cleavage. The oocytes were then moved to fresh G2.2 medium and cultured for an additional 4 days. At the end of eight days, only 2 of the 24 original oocyte denuded controls had reached the morula stage of development. In comparison, 3 of the 16 oocytes which had been vitrified according to the present invention had reached the morula stage of development. In comparison, of the 28 oocytes which had been subjected to vitrification using the OPS methodology, none of them had reached the morula stage of development, with only 4 such oocytes surviving, with the most successful single example of the OPS method having progressed to the 16–32 cell stage.

EXAMPLE 12

Methodologies and Materials for the Vitrification of Mouse and Human Oocytes

A. Media

Media for embryo culture was G1.2 and G2.2 supplemented with 5 mg/ml human serum albumin (Gardner et al., *Hum. Reprod.* 13:3434–40 (1998)). Media for embryo collection and vitrification was a HEPES-buffered modification of G1.2 without EDTA, modified by replacing 20 mM NaHCO$_3$ with 20 mM HEPES and adjusted to pH 7.35.

B. Mice

Oocytes were collected from 4–5 week old F1 (C57BL6xCBa) females. Females were stimulated with 5 iu of pregnant mare's gonadotrophin (Sigma Chemical Co., St. Louis, Mo.) and 53 hr. later with 5 iu of human chorionic gonadotrophin (hCG; Sigma Chemical Co.). Oocytes were collected at 14 hr. post-hCG and denuded from surrounding cumulus by incubation in H-G1.2 with 0.5 mg/ml hyularonidase for less than 1 min. Oocytes were washed twice in H-G1.2 and either inseminated or cryopreserved.

C. Human Oocyte Collection

Patients were stimulated to produce multiple oocytes according to Gardner et al., *Hum. Reprod.* 13:3434–40 (1998). Oocytes were flushed from the follicles and placed into culture at G1.2 for 4 hr. Oocytes were denuded from surrounding cumulus by incubation in G1.2 with hyularonidase. Immature oocytes were then placed into culture in G2.2 with fetal cord serum for 24 hr. Mature MII oocytes were then either allocated to control or were vitrified using the loop.

D. Loop Vitrification of Mouse and Human Oocytes

Oocytes were vitrified using a 2-step loading with cryoprotectants. Initially oocytes were placed in cryoprotectant solution I which contained 10% DMSO and 10% ethylene glycol for 1 min before being transferred to solution II, which contained 20% DMSO and 20% ethylene glycol, 10 mg/ml Ficoll (MW 400,000) and 0.65 M sucrose for around 20 sec. Oocytes were then transferred to the loop that had previously been dipped into solution II to create a thin-film, and plunged directly into liquid nitrogen. By previously submerging the cryovial under liquid nitrogen, the loop containing the oocytes could be plunged into the cryovial containing liquid nitrogen and sealed under liquid nitrogen in one motion. The vials were stored in standard canes.

Oocytes were thawed using a 2-step dilution with sucrose. With the cryovial submerged under liquid nitrogen the vial was opened and the loop containing cells removed from the liquid nitrogen and placed directly into a well of the base medium of H-G1.2 containing 0.25 M sucrose. The oocytes immediately fall from the loop into the thaw solution. Oocytes were moved from this solution after 2 min and transferred to base medium H-G1.2 containing 0.125 M sucrose for a further 3 min. Subsequently, oocytes were washed twice in H-G1.2 for 5 min. and were then returned to culture.

E. In Vitro-Fertilization and Embryo Culture of Mouse Oocytes

Spermatozoa were aspirated from the epididymis of 12–16 week old F1 (C57BL6xCBa) male mice into medium FG1 (as described by Gardner and Lane, 1997, *Hum. Reprod. Update* 3:367–382) supplemented with 1 mg/ml glutathione and 5 mg/ml HSA (Scandinavian IVF Sciences, Gothenburg, Sweden). Spermatozoa were capacitated for 1.5 hr. before insemination. Before oocytes were inseminated, a small hole (5 μM) was made in the zona of the oocytes using a Fertilase 670 nm laser aiming beam and a collimated 1.48 μM laser beam (MTM Medical Technologies, Montreux, Switzerland). Oocytes were placed in 100 μl drops of FG1 and co-incubated with approximately $1 \times 10^4$ sperm for 4 hr. Oocytes were washed twice and cultured in 20 μl drops of G1.2 at 37° C. in 6% $CO_2$, 5% $O_2$ and 89% $N_2$. Fertilization was assessed by the presence of 2-cell embryos the following morning. All 2-cells were moved to fresh drops of G1.2. After 48 hr. culture embryos were washed well in G2.2 and cultured for a further 48 hr. in medium G2.2 to the blastocyst stage.

F. Viability Assessment of Human Oocytes

Viability of human oocytes was assessed by dye-exclusion. Oocytes were placed in H-G1.2 containing 25 μg/ml of propidium iodide for 10 min., then washed in H-G1.2 for 5 min. Oocytes that had not survived the vitrification procedure had positive staining of nuclei material, while surviving oocytes demonstrate no staining.

G. Statistical Analysis

Differences in development among treatments were assessed using linear-logistic regression where the distribution was binomial (Glim 4.0, Numerical Algorithms Group, Oxford, UK). Day of experiment was fitted as a factor. Differences in cell numbers were assessed using Analysis of Variance as both Gaussian normality and equal variances were confirmed. Multiple comparisons between treatments were assessed by Bonferroni's procedure for multiple comparisons.

EXAMPLE 13

Development in Culture of Mouse Oocytes Following Cryopreservation

Oocytes vitrified using the method of the present invention had significantly higher rates of survival compared to oocytes cryopreserved using the slow-freezing procedure, as shown in Table 6. Similarly, fertilization rates were significantly higher in oocytes that were vitrified using the method of the present invention compared to the slow-freezing procedure as shown in Table 6. Oocytes vitrified using the present method had equivalent fertilization rates to control fresh oocytes which were inseminated, as shown in Table 6. Rates of fertilization were significantly lower in oocytes cryopreserved using the slow-freezing procedure as shown in Table 6. Control embryos that were not frozen developed to the blastocyst stage at rates of 70.0% from total oocyte or 95.4% from 2-cell embryos. There was no difference in blastocyst development rates from oocytes that were vitrified using the loop compared to the control oocytes as shown in Table 6. In contrast, rates of blastocyst development from total oocytes or from 2-cell embryos was significantly reduced in oocytes that were cryopreserved by slow-freezing as shown in Table 6.

TABLE 6

Effect of Cryopreservation of Mouse Oocytes on Mouse Fertilization and Embryo Development

| Treatment | Survival (%) | Fertilization (%) | Blastocyst/Total (%) | Blastocyst/2-Cell (%) |
|---|---|---|---|---|
| Control | 100 | 73.4 | 70.0 | 95.4 |
| Loop | 99.2 | 69.8 | 67.4 | 96.5 |
| Slow-freeze | 80.9* | 39.5** | 25.7** | 65.1** |

N = at least 300 embryos per treatment
*significantly different from all other treatments ($P < 0.05$)
**significantly different from all other treatments ($P < 0.01$)

EXAMPLE 14

Subsequent Viability of Mouse Oocytes Following Cryopreservation

Blastocysts derived from either fresh or cryopreserved oocytes (either by vitrification with the present methodology or slow freezing) were transferred to pseudo-pregnant recipients and implantation and fetal development assessed and the results given in Table 7. Blastocysts that were derived from oocytes that were vitrified using the method of the present invention had similar implantation rates to fresh oocytes, however fetal development was slightly lower. In contrast, oocytes that were frozen using the slow-freeze procedure had significantly reduced implantation and fetal development rates compared to either control oocytes or oocytes vitrified using the method of the present invention. Additionally, 2 females which each had 8 blastocysts transferred that resulted from oocytes that were vitrified were allowed to litter. Eleven pups were born from these females (7 and 4) and all developed into morphologically normal and fertile adult mice. Of the eleven pups born, 8 were females and 3 males.

TABLE 7

Effect of Cryopreservation on Mouse Viability Following Transfer

| Treatment | Implantation (%) | Fetal Development (%) | Fetal Development/Implantation (%) |
|---|---|---|---|
| Control | 86[a] | 68.0[a] | 79.1[a] |
| Loop | 88.0[a] | 56.5[b] | 64.2[b] |
| Slow-freeze | 52.4[b] | 26.2[c] | 50.0[b] |

N = at least 50 blastocysts transferred per treatment group
[a–c]different letters are significantly different ($P < 0.05$)

EXAMPLE 15

Survival Rates of Human Oocytes Following Cryopreservation

Viability of human oocytes was assessed following vitrification by the present methodology. High rates of survival were observed, as shown in Table 8.

TABLE 8

Survival Rates of Human Oocytes Following Cryopreservation

| Treatment | Number of Embryos | Survival (%) |
| --- | --- | --- |
| Fresh oocytes | 12 | 100 |
| Vitrified oocytes | 21 | 81.9 |

EXAMPLE 16

Vitrification of Mouse Cleavage Stage Embryos

Embryos were collected according to the methods described in Example 1. One-cell embryos were vitrified using the loop immediately following collection while 2-cell embryos were obtained following 24 hr. culture according to the methods described in Example 1.

One-cell and 2-cell embryos were vitrified using the loop according to the methods described in Example 12. There was no difference in the ability of mouse 1-cell or 2-cell embryos to develop to the blastocyst stage in culture compared to fresh embryos that were not cryopreserved. The results are shown below in Table 9.

TABLE 9

Development of Mouse 1-cell and 2-cell Embryos Following Vitrification According to the Present Invention

| Treatment[#] | Number of Embryos | Blastocyst (%) |
| --- | --- | --- |
| Fresh 1-cells | 20 | 95.0 |
| Vitrified 1-cells | 20 | 90.0 |
| Fresh 2-cells | 30 | 96.7 |
| Vitrified 2-cells | 30 | 93.3 |

[#]There was no difference in the ability of loop vitrified 1-cell or 2-cell embryos to develop in culture compared to fresh embryos.

EXAMPLE 17

Vitrification of Mouse Spermatozoa Using the Present Invention

Mature mouse spermatozoa were collected according to the methods described in Example 12.

A 1 µl drop of cryoprotectant solution I which contained 10% DMSO and 10% ethylene glycol was placed on the lid of a petri dish. A 1 µl of sperm solution was added to the drop of solution I. After 20 sec, 1 µl of solution II, which contained 20% DMSO and 20% ethylene glycol, 10 mg/ml Ficoll (MW 400,000) and 0.65 M sucrose was added and the whole drop placed on a loop which was plunged into liquid nitrogen. For thawing, the loop was placed into a 20 µl of base medium containing 0.25M sucrose for 30 sec., when 20 µl of base medium was added to the drop for a further 1 min, finally 2 ml of base medium was added. Following this procedure, viable sperm could be obtained as determined by motility.

It is understood that the invention is not confined to the particular embodiments set forth herein as illustrative, but embraces all such modified forms thereof as come within the scope of the following claims.

What is claimed is:

1. A kit for the vitrification of a biological specimen, comprising:
    (a) a loop;
    (b) a base medium comprising a cryoprotectant held in the loop; and
    (c) one or more vitrified developmental cells contained in the base medium;
    wherein the one or more vitrified developmental cells are viable upon thawing.

2. The kit of claim 1, further comprising:
    (d) a vial, wherein the vial is of an appropriate size and shape for storing the loop containing the one or more vitrified developmental cells.

3. The kit of claim 1 wherein the loop holds a volume of 1–5 µl.

4. The kit of claim 1 wherein the loop has a width of 20 µm.

5. The kit of claim 1 wherein the loop has a diameter of 0.5 mm to 0.7 mm.

6. The kit of claim 1, further comprising:
    (d) a freezing material in direct contact with the one or more developmental cells.

7. The kit of claim 1 wherein the developmental cells comprise oocytes, morulae or blastocysts.

8. The kit of claim 1 wherein the developmental cells comprise embryos.

9. A kit for the vitrification of a biological specimen, comprising:
    (a) a loop:
    (b) a base medium comprising a cryoprotectant held in the loop:
    (c) one or more developmental cells contained in the base medium; and
    (d) a thaw solution in contact with the loop.

10. A kit for vitrifying a biological specimen, comprising:
    (a) a transfer instrument;
    (b) a thin film of a medium comprising a cryoprotectant, wherein the thin film is held in place by adhesion forces between the medium and the transfer instrument; and
    (c) one or more developmental cells held in the thin film.

11. The kit of claim 10 wherein the transfer instrument encircles the thin film.

12. The kit of claim 10 wherein the developmental cells comprise oocytes, morulae, blastocysts or embryos.

* * * * *